(12) United States Patent
Scavone et al.

(10) Patent No.: US 8,895,041 B2
(45) Date of Patent: Nov. 25, 2014

(54) COMPOSITIONS FOR DELIVERING PERFUME TO THE SKIN

(75) Inventors: Timothy Alan Scavone, Loveland, OH (US); Jianjun Justin Li, West Chester, OH (US); Marc Adam Flickinger, Oakley, OH (US); Jonathan Robert Cetti, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 111 days.

(21) Appl. No.: 13/428,347

(22) Filed: Mar. 23, 2012

(65) Prior Publication Data
US 2013/0252933 A1 Sep. 26, 2013

(51) Int. Cl.
  *A61K 8/73* (2006.01)
  *A61Q 13/00* (2006.01)
  *A61Q 5/02* (2006.01)
  *A61P 17/00* (2006.01)
  *A61K 31/555* (2006.01)
  *A61Q 19/10* (2006.01)

(52) U.S. Cl.
  USPC ............................ 424/401; 514/188; 510/103

(58) Field of Classification Search
  CPC ....... A61K 31/555; A61K 8/73; A61Q 13/00; A61Q 19/10; A61Q 5/02
  USPC ............................ 510/103; 514/188; 424/401
  See application file for complete search history.

(56) References Cited

U.S. PATENT DOCUMENTS

| | | | |
|---|---|---|---|
| 2,438,091 A | 3/1948 | Lynch | |
| 2,528,378 A | 10/1950 | Mannheimer et al. | |
| 2,658,072 A | 11/1953 | Kosmin | |
| 2,809,971 A | 10/1957 | Bernstein et al. | |
| 3,236,733 A | 2/1966 | Karsten et al. | |
| 3,753,196 A | 8/1973 | Kurtz et al. | |
| 3,761,418 A | 9/1973 | Parran, Jr. | |
| 3,819,431 A | 6/1974 | Kurtz et al. | |
| 4,323,683 A | 4/1982 | Bolich, Jr. et al. | |
| 4,345,080 A | 8/1982 | Bolich, Jr. | |
| 4,379,753 A | 4/1983 | Bolich, Jr. | |
| 4,470,982 A | 9/1984 | Winkler | |
| 4,678,598 A * | 7/1987 | Ogino et al. | 510/102 |
| 4,803,195 A | 2/1989 | Holzner | |
| 5,011,681 A | 4/1991 | Ciotti et al. | |
| 5,135,747 A | 8/1992 | Faryniarz et al. | |
| 5,176,903 A | 1/1993 | Goldberg et al. | |
| 5,364,617 A | 11/1994 | Bush et al. | |
| 5,378,468 A | 1/1995 | Suffis et al. | |
| 5,380,707 A | 1/1995 | Barr et al. | |
| 5,384,186 A * | 1/1995 | Trinh | 442/96 |
| 5,462,963 A | 10/1995 | Bush et al. | |
| 5,487,884 A | 1/1996 | Bissett et al. | |
| 5,508,259 A | 4/1996 | Holzner et al. | |
| 5,543,157 A | 8/1996 | Trinh et al. | |
| 5,571,782 A | 11/1996 | Trinh et al. | |
| 5,580,851 A | 12/1996 | Trinh et al. | |
| 5,626,852 A | 5/1997 | Suffis et al. | |
| 5,626,856 A | 5/1997 | Berndt | |
| 5,635,238 A | 6/1997 | Trinh et al. | |
| 5,652,228 A | 7/1997 | Bissett | |
| 5,681,852 A | 10/1997 | Bissett | |
| 5,711,941 A | 1/1998 | Behan et al. | |
| 5,780,020 A | 7/1998 | Peterson et al. | |
| 5,861,144 A | 1/1999 | Peterson et al. | |
| 5,874,067 A | 2/1999 | Lucas et al. | |
| 5,879,666 A | 3/1999 | Lucas et al. | |
| 5,882,638 A | 3/1999 | Dodd et al. | |
| 5,897,855 A | 4/1999 | Trinh et al. | |
| 5,932,198 A | 8/1999 | Goldman et al. | |
| 5,932,199 A | 8/1999 | Esser | |
| 6,036,964 A | 3/2000 | Guenin et al. | |
| 6,068,834 A | 5/2000 | Kvalnes et al. | |
| 6,110,449 A | 8/2000 | Bacon et al. | |
| 6,123,932 A | 9/2000 | Guskey et al. | |
| 6,165,452 A | 12/2000 | Boden et al. | |
| 6,180,121 B1 | 1/2001 | Guenin et al. | |
| 6,217,888 B1 | 4/2001 | Oblong et al. | |
| 6,238,678 B1 | 5/2001 | Oblong et al. | |
| 6,306,818 B1 | 10/2001 | Anderson et al. | |
| 6,395,691 B1 | 5/2002 | Tsaur | |
| 6,495,097 B1 | 12/2002 | Streit et al. | |
| 6,509,010 B2 | 1/2003 | Beck et al. | |
| 6,635,702 B1 | 10/2003 | Schmucker-Castner et al. | |
| 6,645,511 B2 | 11/2003 | Aronson et al. | |
| 6,716,440 B2 | 4/2004 | Aronson et al. | |
| 6,759,376 B2 | 7/2004 | Zhang et al. | |
| 6,780,826 B2 | 8/2004 | Zhang et al. | |
| 6,793,915 B1 | 9/2004 | Guenin et al. | |
| 6,805,855 B2 | 10/2004 | Mattai et al. | |
| 6,835,373 B2 | 12/2004 | Kolodzik et al. | |
| 6,869,923 B1 | 3/2005 | Cunningham et al. | |
| 6,893,647 B1 | 5/2005 | Malton et al. | |
| 6,897,253 B2 | 5/2005 | Schmucker-Castner et al. | |
| 7,119,059 B2 | 10/2006 | Librizzi et al. | |
| 7,208,462 B2 | 4/2007 | Heltovics et al. | |
| 7,208,463 B2 | 4/2007 | Heltovics et al. | |
| 7,208,464 B2 | 4/2007 | Heltovics | |
| 7,235,261 B2 | 6/2007 | Smith et al. | |

(Continued)

FOREIGN PATENT DOCUMENTS

| | | |
|---|---|---|
| EP | 0758882 B1 | 1/2003 |
| WO | 95/07432 | 3/1995 |
| WO | 98/18439 A1 | 5/1998 |
| WO | 98/56340 A1 | 12/1998 |

OTHER PUBLICATIONS

International Search Report PCT/US2013/033234 mailed Mar. 18, 2014 including Written Opinion of the International Searching Authority, 11 pages.

*Primary Examiner* — Audrea Buckley
(74) *Attorney, Agent, or Firm* — Carlos A. Garcia; Mark A. Charles

(57) ABSTRACT

A cleansing composition comprising at least 5% of a surfactant, at least about 25% water, a cyclodextrin complex comprising a perfume, wherein 80% of the plurality of perfume raw materials comprise a FDV of at least 0.69.

21 Claims, 1 Drawing Sheet

(56) References Cited

U.S. PATENT DOCUMENTS

| | | |
|---|---|---|
| 7,311,898 B2 | 12/2007 | Tang et al. |
| 7,316,860 B2 | 1/2008 | Yasumoto et al. |
| 7,511,003 B2 | 3/2009 | Focht et al. |
| 7,910,144 B2 | 3/2011 | Ballevre et al. |
| 8,124,573 B2 | 2/2012 | Focht et al. |
| 8,147,808 B2 | 4/2012 | Scavone et al. |
| 8,147,853 B2 | 4/2012 | Taylor et al. |
| 8,431,520 B2 | 4/2013 | Smets et al. |
| 2003/0194416 A1 | 10/2003 | Shefer et al. |
| 2003/0230205 A1 | 12/2003 | Mutschler et al. |
| 2003/0235545 A1 | 12/2003 | Guenin et al. |
| 2004/0091435 A1 | 5/2004 | Shefer et al. |
| 2004/0109833 A1 | 6/2004 | Tang et al. |
| 2004/0175404 A1 | 9/2004 | Shefer et al. |
| 2004/0202632 A1 | 10/2004 | Gott et al. |
| 2004/0223991 A1 | 11/2004 | Wei et al. |
| 2005/0003975 A1 | 1/2005 | Browne et al. |
| 2005/0100570 A1 | 5/2005 | Wei et al. |
| 2006/0079422 A1* | 4/2006 | Midha et al. ............ 510/130 |
| 2006/0159639 A1 | 7/2006 | Ogura et al. |
| 2006/0243322 A1 | 11/2006 | Heltovics et al. |
| 2006/0263311 A1 | 11/2006 | Scavone et al. |
| 2006/0263312 A1 | 11/2006 | Scavone et al. |
| 2006/0263313 A1 | 11/2006 | Scavone et al. |
| 2006/0292098 A1 | 12/2006 | Scavone et al. |
| 2007/0248553 A1 | 10/2007 | Scavone et al. |
| 2008/0039353 A1 | 2/2008 | Focht et al. |
| 2008/0045428 A1 | 2/2008 | Focht et al. |
| 2008/0045429 A1 | 2/2008 | Focht et al. |
| 2008/0085440 A1 | 4/2008 | Yasumoto et al. |
| 2008/0194454 A1 | 8/2008 | Morgan et al. |
| 2008/0213191 A1 | 9/2008 | Scavone et al. |
| 2008/0213203 A1 | 9/2008 | Seavone et al. |
| 2008/0213204 A1 | 9/2008 | Scavone et al. |
| 2008/0215023 A1 | 9/2008 | Scavone et al. |
| 2010/0087357 A1 | 4/2010 | Morgan, III et al. |
| 2010/0137178 A1 | 6/2010 | Smets et al. |
| 2011/0212147 A1 | 9/2011 | Scavone et al. |
| 2011/0212148 A1 | 9/2011 | Scavone et al. |

* cited by examiner

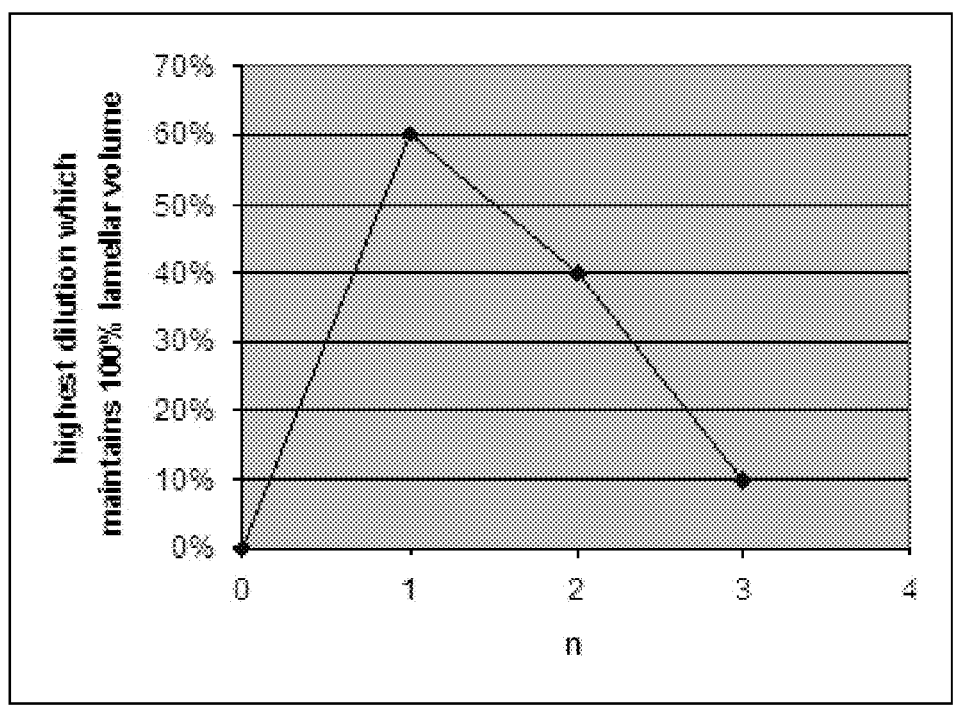

COMPOSITIONS FOR DELIVERING PERFUME TO THE SKIN

BACKGROUND OF THE INVENTION

Cleansing the skin is an activity that has been done for millennia. Over time, skin cleansing and related methods for cleansing skin have involved the utilization of soap, surfactants, and the like. Today, one prevalent form of skin cleansing compositions is the liquid form, often known as body wash. Users of body wash enjoy the conveniences that these compositions offer; however, the experience is not ideal. As the compositions for cleaning skin have evolved, the problems associated with these compositions have not. Many of the issues associated with current compositions and methods for skin cleansing, particularly body wash compositions, have not been addressed, and remain issues for users of these products today.

Perfumes are often associated with body washes. These perfumes perform a number of tasks. Perfumes within a body wash composition cover and/or mask the smell of a body wash composition with a scent pleasing to a user. Perfumes within a body wash composition also signal the efficacy of the product to a user. Additionally, perfumes within a body wash composition are delivered, in very small quantities, to the skin.

While perfumes within a body wash are delivered to the skin, the delivery of these compositions is executed rather poorly. The vast majority of the perfume within the body wash composition is rinsed away during the cleansing of the user, leaving very little perfume deposited on the skin to provide a benefit to the user. Moreover, the benefit to the user of this perfume deposition is not maximized, as the release of these materials begins immediately after deposition, presumably while the user is still fresh from the associated cleansing.

As such, there is a need to provide a body wash with a perfume composition that is long lasting. Specifically, there is a need to provide a body wash with a perfume composition that deposits more efficiently and is capable of lasting beyond the initial cleansing of the user. This invention addresses these needs.

SUMMARY OF THE INVENTION

In one embodiment, there is a cleansing composition comprising at least 5% of a surfactant, at least about 25% water, a cyclodextrin complex comprising a perfume, said perfume comprising a plurality of perfume raw materials, at least one of which is selected from Iso-E_Super, methyl ionone, a-Irone, gamma_methyl_ionone, Labienone Oxim, Cashmeran, delta-damascone, beta-Ionone, Dihydro-beta-ionone, Damascenone, _trans-, and alpha-Damascone wherein 80% of the plurality of perfume raw materials comprise a FDV of at least 0.70. In an alternate embodiment, there is a cleansing composition for delivering a dilution triggered bloom of a perfume comprising: at least 5% of a surfactant, at least about 25% water a cyclodextrin complex comprising a perfume, said perfume comprising perfume raw materials, at least one of which comprises a FDV of at least about 0.70 wherein the ratio of water to cyclodextrin complex is between about 15:1 and 1:1, wherein the cleansing composition comprises a ARDON value of at least 130%. In yet another embodiment, there is a cleansing composition comprising at least 5% of a surfactant, at least about 25% water, a cyclodextrin complex comprising a perfume, said perfume comprising a plurality of perfume raw materials, at least one of which is selected from Iso-E_Super, methyl ionone, a-Irone, gamma_methyl_ionone, Labienone Oxim, Cashmeran, delta-damascone, beta-Ionone, Dihydro-beta-ionone, Damascenone, _trans-, and alpha-Damascone, wherein 80% of the plurality of perfume raw materials comprise a FDV of at least 0.70, wherein the ratio of water to cyclodextrin complex is between about 15:1 and 1:1, wherein the cleansing composition comprises a ARDON value of at least 130%. In yet another embodiment, there is a cleansing composition comprising: at least 5% of a surfactant, at least about 25% water, a cyclodextrin complex comprising a perfume, said perfume comprising a plurality of perfume raw materials, at least one of which is selected from Iso-E_Super, methyl ionone, a-Irone, gamma_methyl_ionone, Labienone Oxim, Cashmeran, delta-damascone, beta-Ionone, Dihydro-beta-ionone, Damascenone, _trans-, and alpha-Damascone, wherein the cyclodextrin complex has a degree of complexation of at least 90% prior to incorporation into the cleansing composition.

BRIEF DESCRIPTION OF THE DRAWINGS

FIG. 1 is a graph illustrating dilution related to lamellar volume.

DETAILED DESCRIPTION OF THE INVENTION

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While the specification concludes with the claims particularly pointing and distinctly claiming the invention, it is believed that the present invention will be better understood from the following description.

The devices, apparatuses, methods, components, and/or compositions of the present invention can include, consist essentially of, or consist of, the components of the present invention as well as other ingredients described herein. As used herein, "consisting essentially of" means that the devices, apparatuses, methods, components, and/or compositions may include additional ingredients, but only if the additional ingredients do not materially alter the basic and novel characteristics of the claimed devices, apparatuses, methods, components, and/or compositions.

All percentages and ratios used herein are by weight of the total composition and all measurements made are at 25° C., unless otherwise designated.

All measurements used herein are in metric units unless otherwise specified.

The term "anhydrous" as used herein, unless otherwise specified, refers to those compositions or materials containing less than about 10%, more preferably less than about 5%, even more preferably less than about 3%, even more preferably zero percent, by weight of water.

The term "multiphase" as used herein means that compositions comprise at least two phases which are chemically distinct (e.g. a surfactant phase and a benefit phase). Such phases are in direct physical contact with one another and are not separated by a barrier. In one aspect of the invention, the personal care composition can be a multiphase personal care composition where the phases of the personal care composition are blended or mixed to a significant degree. In another aspect of the invention, the personal care composition can be a multiphase personal care composition where the phases of the personal care composition are made to occupy separate but distinct physical spaces inside the package in which they are stored, but are in direct contact with one another (i.e., they are not separated by a barrier and they are not emulsified or mixed to any significant degree).

The term "package" includes any suitable container for a personal care compositions exhibiting a viscosity from about 1,500 centipoise (cP) to about 1,000,000 cP, including but not limited to bottle, tottle, tube, jar, non-aerosol pump and mixtures thereof.

The term "personal care composition" as used herein, refers to compositions intended for topical application to the skin or hair. The compositions of the present invention are rinse-off formulations, in which the product is applied topically to the skin or hair and then is subsequently rinsed within minutes from the skin or hair with water, or otherwise wiped off using a substrate with deposition of a portion of the composition. The compositions also may be used as shaving aids. The personal care composition of the present invention is typically extrudable or dispensible from a package. The multiphase personal care compositions typically exhibit a viscosity of from about 1,500 centipoise (cP) to about 1,000,000 cP, as measured by as measured by the Viscosity Method as described in the commonly owned, patent application published on Nov. 11, 2004 under U.S. Publication No. 2004/0223991A1 entitled "Multi-phase Personal Care Compositions" filed on May 7, 2004 by Wei, et al. The multiphase personal care compositions of the present invention can be in the form of liquid, semi-liquid, cream, lotion or gel compositions intended for topical application to skin. Examples of personal care compositions of the present invention can include but are not limited to shampoo, conditioning shampoo, body wash, moisturizing body wash, shower gels, skin cleansers, cleansing milks, hair and body wash, in shower body moisturizer, pet shampoo, shaving preparations and cleansing compositions used in conjunction with a disposable cleansing cloth.

The phrase "substantially free of" as used herein, unless otherwise specified means that the composition comprises less than about 5%, preferably less than about 3%, more preferably less than about 1% and most preferably less than about 0.1% of the stated ingredient. The term "free of" as used herein means that the composition comprise 0% of the stated ingredient that is the ingredient has not been added to the composition, however, these ingredients may incidentally form as a byproduct or a reaction product of the other components of the composition.

The term "stable," as used herein, means that the multiphase personal care composition comprises less than 10% "third-phase" volume, more preferably less than 5% "third-phase" volume, most preferably less than 1% "third-phase" volume after undergoing the rapid protocol aging and third phase measurement as described below in the "Third-Phase" Method.

The term "structured," as used herein means having a rheology that confers stability on the multiphase composition. The degree of structure is determined by characteristics determined by one or more of the following methods: the Young's Modulus Method, Yield Stress Method, or the Zero Shear Viscosity Method or by the Ultracentrifugation Method, all in the Test Methods below. Accordingly, a surfactant phase of the multiphase composition of the present invention is considered "structured," if the surfactant phase has one or more of the following properties described below according to the Young's Modulus Method, Yield Stress Method, or the Zero Shear Viscosity Method or by the Ultracentrifugation Method. A surfactant phase is considered to be structured, if the phase has one or more of the following characteristics:

A. a Zero Shear Viscosity of at least about 100 Pascal-seconds (Pa-s), alternatively at least about 200 Pa-s, alternatively at least about 500 Pa-s, alternatively at least about 1,000 Pa-s, alternatively at least about 1,500 Pa-s, alternatively at least about 2,000 Pa-s; or B. a Structured Domain Volume Ratio as measured by the Ultracentrifugation Method described hereafter, of greater than about 40%, preferably at least about 45%, more preferably at least about 50%, more preferably at least about 55%, more preferably at least about 60%, more preferably at least about 65%, more preferably at least about 70%, more preferably at least about 75%, more preferably at least about 80%, even more preferably at least about 85%; or most preferably at least about 90%.

C. A Young's Modulus of greater than about 2 Pascal (Pa), more preferably greater than about 10 Pa, even more preferably greater than about 20 Pa, still more preferably greater than about 30 Pa, 40 Pa, 50 Pa, 75 Pa, most preferably greater than 100 Pa.

The term "surfactant component" as used herein means the total of all anionic, nonionic, amphoteric, zwitterionic and cationic surfactants in a phase. When calculations are based on the surfactant component, water and electrolyte are excluded from the calculations involving the surfactant component, since surfactants as manufactured typically are diluted and neutralized.

The term "STnS" as used herein, means sodium trideceth sulfate, where n is defined as the average number of moles of ethoxylate per molecule. Trideceth is a 13 carbon branched ethoxylated hydrocarbon comprising, in one embodiment, an average of at least 1 methyl branch per molecule.

The term "SLS" as used herein, means sodium lauryl sulfate.

The term "lather" as used herein, means the aerated foam which results from providing energy to aqueous surfactant mixtures, especially dilute mixtures. Lather is increased in micellar compositions compared to structured, e.g., lamellar compositions, so that a phase change during dilution to micelles typically increases lather.

As used herein "tottle" refers to a bottle which rests on neck or mouth which its contents are filled in and dispensed from, but it is also the end upon which the bottle is intended to rest or sit upon (e.g., the bottle's base) for storage by the consumer and/or for display on the store shelf (this bottle is referred to herein as a "tottle"). Typically, the closure on a tottle is flat or concave, such that the tottle, when stored, rests on the closure. Suitable tottles are described in the co-pending U.S. patent application Ser. No. 11/067,443 filed on Feb. 25, 2005 to McCall, et al, entitled "Multi-phase Personal Care Compositions, Process for Making and Providing, and Article of Commerce."

The term "visually distinct" as used herein, refers to a region of the multiphase personal care composition having one average composition, as distinct from another region having a different average composition, wherein the regions are visible to the unaided naked eye. This would not preclude the distinct regions from comprising two similar phases where one phase could comprise pigments, dyes, particles, and various optional ingredients, hence a region of a different average composition. A phase generally occupies a space or spaces having dimensions larger than the colloidal or sub-colloidal components it comprises. A phase can also be constituted or re-constituted, collected, or separated into a bulk phase in order to observe its properties, e.g., by centrifugation, filtration or the like.

One embodiment of the current invention relates to a cleansing composition comprising at least about 5% of a surfactant, at least about 25% water, and a cyclodextrin complex comprising a perfume composition, said perfume composition comprising at least one perfume raw material selected from Iso-E_Super, methyl ionone (Xandralia), a-Irone, gamma_methyl_ionone, 10% Labienone Oxim (labienoxime) in DPG, Cashmeran, delta-damascone, beta-Ionone, Dihydro-beta-ionone, Damascenone, _trans-, and alpha-Damasconehere, wherein the complex has a degree of complexation of at least 90% prior to incorporation into the body wash formulation, wherein 80% of the perfume raw materials have a degree of complex retention greater than 50% after incorporation into the body wash composition, wherein the ratio of water to cyclodextrin complex is between about 15:1 and 1:1 within the body wash composition.

With out wishing to be bound by theory, it is believed that cyclodextrin-fragrance complexes release based on a dilution ratio (ratio of water:cyclodextrin-fragrance complex). Surprisingly, we have found that the dilution ratio required for release of a fragrance is high enough as to enable formulation of a stable neat fragrance complex in an aqueous surfactant environment yet release on further dilution in the shower (to create the surprising effect of changing fragrance character during the shower) or releasing much later in the day on skin. The ability to tailor release by the effect desired is highly dependent on the perfume molecule choice and the strength of the cyclodextrin complex formed. The strength of the complex formed requires that one start with a fragrance molecule that is highly bound using a complex formation technology that achieves a high degree of complexation and second, requires the selection of perfume molecules with a high binding affinity within the cyclodextrin cavity. The binding affinity of fragrance molecules within the cyclodextrin cavity is governed by how well the perfume molecule fits (based on molecule size, shape and chemical affinity for the interior of the cyclodextrin cavity). We have learned that with careful selection of perfume molecules, we can tailor this release to deliver the desired consumer effects through choiceful selection of high binding fragrance molecules that are formed using a complexation technology that highly binds the materials.

Without wishing to be bound by theory, there is another example where manipulation of the binding affinity of cyclodextrin is useful. This is in the case where it is desired to hide a high odor compound even through the dilution stage, yet still deliver on dilution the ability to activate sensory receptors in the scalp. One such highly useful combination is when menthol and cyclodextrin are complexed and incorporated into antidandruff products.

For example in the case of hair care products, including those containing zinc pyridinethione, when menthol is complexed with cyclodextrin, because of the high binding affinity of the complex in a shampoo, the menthol is relatively odorless. Surprisingly, while the "tingling" effect of menthol can be felt on the scalp during/after application, there is no smell of menthol. Thus, this complex surprisingly indicates efficacy vis-à-vis the tingling effect, with none of the negative menthol smell. This tingling sensation is unique because it signals efficacy on the surface of the scalp, which is particularly useful for antidandruff products, without the negative menthol smell, which limits the commercial utility of using menthol broadly in Hair care products.

Perfume Raw Materials

The perfume of the present invention comprises perfume raw materials (PRMs) that are retained by the cyclodextrin complex. PRMs of the present invention comprise a Fractional Delivery Value (FDV) of at least about 0.69, alternatively at least about 0.80. Table 1 includes a list of acceptable (PRMs) of the present invention along with the Fractional Delivery Values (FDF) of the PRMs. In an alternate embodiment, the PRMs of the present invention include Iso-E_Super, methyl ionone (Xandralia), a-Irone, gamma_methyl_ionone, 10% Labienone Oxim (labienoxime) in DPG, Cashmeran, delta-damascone, beta-Ionone, Dihydro-beta-ionone, Damascenone, _trans-, and alpha-Damascone, all of which have a FDV at least about 0.70.

Exemplary PRM and their associated FDV are in Table 1, below. One of ordinary skill would readily know that this list is not exhaustive and that there may be additional PRM's having an FDV of at least about 0.69.

TABLE 1

| Perfume Raw Material | FDV |
|---|---|
| Sclareol oxide | 0.88 |
| Kephalis | 0.86 |
| Maltyl_isobutyrate | 0.84 |
| Floramat | 0.83 |
| Cyclohexanecarboxylic_acid,_2,2,6-trimethyl-,_ethyl_ester,_(1R,6S)-rel- | 0.82 |
| Patchouli_alcohol | 0.81 |
| o-tert-Butylcyclohexyl_acetate (verdox) | 0.81 |
| Givescone | 0.81 |
| 3,6-Dimethyl-3-octanyl_acetate | 0.81 |
| Acetic_acid,_hexylene_glycol | 0.81 |
| Thujopsene | 0.80 |
| (+)-D-Menthyl_acetate | 0.80 |
| Isomenthyl_acetate | 0.80 |
| Menthyl acetate; | 0.80 |
| dl-MENTHYL_ACETATE | 0.80 |
| Menthyl_Acetate | 0.80 |
| Tetrahydrolinalyl_acetate | 0.80 |
| Alicate | 0.80 |
| Dihydroterpinyl_acetate | 0.80 |
| Rosamusk | 0.79 |
| Amber_acetate | 0.79 |
| Butylated_hydroxytoluene | 0.79 |
| Koavone | 0.79 |
| 3-Thujopsanone | 0.78 |
| alpha-Himachalene | 0.78 |
| beta-Himachalene | 0.78 |
| Ethyl beta-safranate | 0.78 |
| Ethyl_gamma-Safranate | 0.78 |
| Ethyl_alpha-safranate | 0.78 |
| alpha-Terpinyl_Acetate | 0.78 |
| gamma-Himachalene | 0.78 |
| beta-Himachalene Oxide | 0.78 |
| Vertenex | 0.77 |
| 4-tert.Butylcyclohexylacetate | 0.77 |
| alpha-Terpinyl propionate | 0.77 |
| Trichloromethyl_phenyl_carbinyl_acetate | 0.77 |
| alpha-COPAENE | 0.77 |
| g-Terpineol_acetate | 0.77 |
| Vanoris | 0.77 |
| Sclareolate | 0.77 |
| Iso-E_Super | 0.77 |
| .beta.-Georgywood | 0.77 |
| Caryolan-1-ol | 0.77 |
| Boisiris | 0.77 |
| 2-isopropyl-N,2,3-trimethylbutyramide | 0.76 |
| Selina-3,7(11)-diene | 0.76 |
| Zonarene | 0.76 |
| Delta Amorphene | 0.76 |
| delta-Cadinene | 0.76 |

TABLE 1-continued

| Perfume Raw Material | FDV |
|---|---|
| beta-Copaene | 0.76 |
| Bigarade oxide | 0.76 |
| tobacco dodecane | 0.76 |
| Dihydrocarveol acetate | 0.76 |
| alpha-Cadinene | 0.76 |
| alpha-Muurolene | 0.76 |
| alpha-Amorphene | 0.76 |
| Valerianol | 0.75 |
| gamma-Eudesmol | 0.75 |
| 10-epi-gamma-Eudesmol | 0.75 |
| Hexyl Neopentanoate | 0.75 |
| beta-Terpinyl acetate | 0.75 |
| Octalynol | 0.75 |
| alpha-Cadinol | 0.75 |
| tau-Muurolol | 0.75 |
| tau-Cadinol | 0.75 |
| Tetrahydroionol | 0.75 |
| 7-eip-alpha-Eudesmol | 0.75 |
| alpha-Eudesmol | 0.75 |
| delta-Elemene | 0.75 |
| Clarycet | 0.75 |
| Isopentyrate | 0.75 |
| Valencene | 0.75 |
| Linalyl isobutyrate | 0.74 |
| 7-epi-alpha-Selinene | 0.74 |
| alpha-Selinene | 0.74 |
| gamma-Muurolene | 0.74 |
| gamma-Cadinene | 0.74 |
| beta-Caryophyllene | 0.74 |
| Ozofleur | 0.74 |
| Elemol | 0.74 |
| Linalyl acetate | 0.74 |
| Herbavert | 0.74 |
| 7-Acetyl-1,1,3,4,4,6-hexamethyltetralin | 0.74 |
| Isoamyl isobutyrate | 0.74 |
| Linalyl propionate | 0.74 |
| Methyl Camomille | 0.74 |
| Carvyl acetate | 0.74 |
| alpha-Humulene | 0.73 |
| Germacrene B | 0.73 |
| alpha,4-Dimethyl benzenepropanal | 0.73 |
| alpha-Isomethylionone | 0.73 |
| Isoamyl angelate | 0.73 |
| Frutinat | 0.73 |
| Oxyoctaline formate | 0.73 |
| Lavandulyl acetate | 0.73 |
| beta-Selinene | 0.73 |
| Isopropyl 2-methylbutyrate | 0.73 |
| Dihydro-beta-ionone | 0.73 |
| Floralate | 0.73 |
| Cashmeran | 0.73 |
| N-ethyl-p-menthane-3-carboxamide | 0.72 |
| a-Iron | 0.72 |
| Isobutyl angelate | 0.72 |
| Hexyl 2-methylbutanoate | 0.72 |
| Dihydro-alpha-ionone | 0.72 |
| Timberol | 0.72 |
| Isobutyl caproate | 0.72 |
| beta-Damascone (E-configuration) | 0.72 |
| beta-Damascone | 0.72 |
| alpha-Vetivone | 0.72 |
| Hexyl isobutyrate | 0.72 |
| Dimethyl Octanyl Acetate | 0.72 |
| gamma methyl ionone | 0.72 |
| Linalyl butyrate | 0.72 |
| Herboxane | 0.72 |
| Cetonal | 0.72 |
| Grisalva | 0.72 |
| 1-(2,6,6-Trimethyl-2-cyclohexen-1-yl)-2-buten-1-one | 0.71 |
| alpha-Damascone | 0.71 |
| Nopyl acetate | 0.71 |
| p-tert-Amyl cyclohexanol | 0.71 |
| alpha-Bergamotene | 0.71 |
| Isopentyl butyrate | 0.71 |
| delta-damascone | 0.71 |
| Germacrene D | 0.71 |
| 1,1,2,3,3-Pentamethylindan | 0.71 |
| Rossitol | 0.71 |
| Myrcenyl acetate | 0.71 |
| Datilat | 0.71 |
| Undecanolide | 0.71 |
| Pentanoic acid, 2-methyl-, ethyl ester (manzanate) | 0.71 |
| Eucalyptol | 0.70 |
| beta-Ionone | 0.70 |
| Beta ionone epoxide | 0.70 |
| 4-tert-Amylcyclohexanone | 0.70 |
| Tetrahydrolinalool (Tetrahydro Linalool) | 0.70 |
| Amber butanol (Amber Core) | 0.70 |
| Vetikol acetate | 0.70 |
| Hexyl tiglate | 0.70 |
| gamma-Damascone | 0.70 |
| Nootkatone | 0.70 |
| alpha-Ionone | 0.70 |
| trans-2-tert-Butylcyclohexanol | 0.70 |
| Verdol | 0.70 |
| Wolfwood | 0.70 |
| Pomarose | 0.70 |
| 6,8-dimethyl-2-nonanol | 0.70 |
| Jasmal | 0.70 |
| methyl ionone (Xandralia) | 0.70 |
| cis-3-Hexenyl 2-methylbutyrate | 0.70 |
| Tetrahydromyrcenol | 0.70 |
| Maceal | 0.70 |
| Diethyl malonate | 0.70 |
| Citronellyl acetate | 0.70 |
| Dimethylbenzylcarbinylacetate | 0.70 |
| delta-Decalactone | 0.70 |
| Methyl-beta-ionone | 0.70 |
| Boronal | 0.70 |
| 10% Labienone Oxim (labienoxime) in DPG | 0.70 |
| Damascenone, trans- | 0.70 |
| 2-Buten-1-one, 1-(2,6,6-trimethyl-1,3-cyclohexadien-1-yl)- | 0.70 |
| Caryophyllene alcohol acetate | 0.70 |
| Isodamascone | 0.70 |
| Ethyl 3,7-dimethyl-2,6-octadienoate | 0.69 |
| Gelsone | 0.69 |
| Cyclemone A | 0.69 |
| delta-Undecalactone | 0.69 |
| Isopentyl propanoate | 0.69 |
| Verdural B Extra | 0.69 |
| 5-Acetyl-1,1,2,3,3,6-hexamethylindan | 0.69 |
| Diethyl phthalate | 0.69 |
| Veltonal | 0.69 |
| alpha-methyl ionone | 0.69 |
| Menthone 1,2-glycerol ketal (racemic) | 0.69 |
| Dihydro Terpineol | 0.69 |
| Patchone | 0.69 |
| Ethyl octanoate | 0.69 |
| Limetol | 0.69 |
| Oxane | 0.69 |
| alpha-Agarofuran | 0.69 |
| n-Pentyl butyrate | 0.69 |
| para-Menthane | 0.69 |
| Phellandrene | 0.69 |
| Cyclohexane, 1-methyl-4-(1-methylethyl)-, cis- | 0.69 |
| 3-Hexenyl isovalerate | 0.69 |
| Menthol | 0.69 |
| Cyclohexanol, 5-methyl-2-(1-methylethyl)-, (1.al | 0.69 |
| neo-Menthol | 0.69 |
| (+)-D-Menthol | 0.69 |
| (−)-Menthol | 0.69 |
| d-Neomenthol | 0.69 |
| Isononyl acetate | 0.69 |

TABLE 1-continued

| Perfume Raw Material | FDV |
| --- | --- |
| cis-Pinane | 0.69 |
| Ethyl_heptoate (Ethyl Oenanthate) | 0.69 |
| Tabanone | 0.69 |
| 3,5,5-Trimethyl-1-hexanol | 0.69 |
| p-Cresyl_isobutyrate | 0.69 |

It is contemplated that PRMs having a FDV of lower than about 0.69 (L-PRM) may be used in combination with PRMs having a FDV of at least about 0.69 (H-PRM). Such a configuration enables the delivery of L-PRMs before a dilution triggered step, as these materials are less bound to the cyclodextrin. As such, the delivery of materials can be controlled within a perfume and product, depending on the characteristics desired for the perfume delivery. When staged delivery of PRMs is desired, the ratio of H-PRM to L-PRM is between about 1:2 to about 2:1, alternatively between about 1:4 and 4:1.

The ARDON test has been developed as a mechanism to determine whether the overall perfume release mechanism utilizes complexed cyclodextrins within a body wash chassis. In this way, the presence of PRMs with sufficiently high FDV values can be determined without the need to test for each individual PRM to determine its presence or without knowing the final formulation of the end product. Without wishing to be bound by theory, it is believed that the dilution of the product when containing cyclodextrin and H-PRMs results in a significantly higher ARDON value than products without either cyclodextrin or H-PRMs within their chassis. This mechanism allows for the testing of products to determine the delivery mechanisms without needing to know the chemical composition of the product. The current invention utilizes compositions having an ARDON value of at least about 130%, alternatively at least about 140%, alternatively at least about 150%.

Surfactant Phase

One of the phases of the personal care composition of the present invention is a surfactant phase. The sufactant phase is comprised of a structured domain that comprises a surfactant and optionally a cosurfactant. The structured domain is preferably an opaque structured domain, which is preferably a lamellar phase. The lamellar phase can provide resistance to shear, adequate yield to suspend particles and droplets and at the same time provides long term stability, since it is thermodynamically stable. The lamellar phase tends to have a viscosity that minimizes the need for viscosity modifiers.

In one embodiment, the personal care compositions of the present invention comprise from about 3% to about 20% STnS, alternatively from about 5% to about 15% STnS, alternatively from about 7% to about 13% STnS, alternatively from about 5% to about 13% STnS, alternatively from about 1% to about 13% STnS.

It has been discovered that STnS having fewer than 3 moles of ethoxylation provides surprising structural improvements. FIG. 1 illustrates these improvements by comparing a composition comprising, ST1S, ST2S, and ST3S. At increasing levels of dilution, ST3S begins to transition from a lamellar structure to a micellar structure beginning at about the 19% surfactant level. As such, dilution beyond this level results in a loss of structure. This loss of structure has, until now, necessitated higher concentrations of surfactant to be present within a package. ST2S compositions can remain well structured until a dilution point of 13% surfactant within this example, allowing for the transition to a more micellar structure at much higher dilution levels. ST1S compositions can remain lamellar at even lower surfactant concentrations.

While sodium trideceth sulfate has been disclosed and commercialized, the utilization and benefits of sodium trideceth sulfate having lower ethoxylation values have been unknown, a rationale further supported by the general popularity of ST3S within commercially available products, and the lack of commercial availability of lower ethoxylation products. It is this unknown and surprising result that enables various benefits of the personal care compositions of the present invention, including improved stability, mildness, compatibility, and lather creation.

Without intending to be limited by theory, the rationale for improved function of STnS, where n is below 3, can be illustrated utilizing dissipative particle dynamics (DPD) simulations. As related to STnS, surfactant aggregates form curved surfaces based on the surfactant shape and interactions between molecules, leading to surfactant architectures which are phases; and to degree of structure of a phase as measured by rheology parameters such as zero shear viscosity. To measure the amount of surfactant curvature, molecular simulations were carried out using DPD by breaking surfactant atoms into beads, where a bead represents typically 3-4 heavy atoms. Simulations were performed in a cube cell with an edge length of approximately 25 nm. The compositions of the simulation boxes varied in average amount of ethoxylation (n=0 to 3) of STnS. Assembly of surfactants into aggregates starting from random positions was observed during the course of the simulations. DPD Curvature was computed as an average curvature over multiple independent simulations for the surfactant head group-water surface of all resulting objects in a simulation frame, including all bilayers and micelles, and is a relative measure of the average deviation of the colligative surfactant head group surface from flat. DPD Curvature of zero are flat layers with edge defects, which do not form multilamellar vesicles and hence are not expected to exhibit structured rheology, e.g., high zero shear viscosity. At DPD Curvature of about 0.07 and higher, elongated micelle structures are observed to form. At intermediate DPD curvature, curved bilayers can form multilamellar vesicles, leading to high zero shear viscosity and stable compositions.

Often, STnS is combined with SLS in order to form a surfactant system. In one embodiment, the personal care compositions of the present invention comprise less than about 5% SLS, alternatively less than about 4% SLS, alternatively less than about 3% SLS, alternatively less than about 2% SLS, alternatively less than about 1% SLS, alternatively between about 0.1% SLS and about 2% SLS, alternatively about 0% SLS. Without wishing to be bound by theory, it is believed that the presence of SLS increases the harshness of the personal care composition, negating at least in part the mildness benefits and/or the efficacy of the benefit agents within the personal care composition.

Cosurfactant

The personal care compositions of the present invention further comprises a cosurfactant. Cosurfactants in the present invention comprise from about 0.1% to 20%, alternatively from about 2% to about 10% of the personal care composition. Cosurfactants of the present invention comprise amphoteric surfactants, zwitterionic surfactants, and mixtures thereof. In one embodiment, the personal care composition comprises at least one amphoteric surfactant. Amphoteric surfactant suitable for use in the present invention include those that are broadly described as derivatives of aliphatic secondary and tertiary amines in which the aliphatic radical can be straight or branched chain and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecyl-aminopropionate, sodium 3-dodecylaminopropane sulfonate, sodium lauryl sarcosinate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and the products described in U.S. Pat. No. 2,528, 378. In one aspect, the multiphase personal care composition can comprise an amphoteric surfactant that is selected from the group consisting of sodium lauroamphoacetate, sodium cocoamphoactetate, disodium lauroamphoacetate disodium cocodiamphoacetate, and mixtures thereof. Moreover, amphoacetates and diamphoacetates can also be used.

Zwitterionic surfactants suitable for use include those that are broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group, e.g., carboxy, sulfonate, sulfate, phosphate, or phosphonate. Zwitterionic surfactants suitable for use in the multiphase, personal care composition include betaines, including cocoamidopropyl betaine.

Associative Polymer

In one embodiment, the associative polymer is a crosslinked, alkali swellable, associative polymer comprising acidic monomers and associative monomers with hydrophobic end groups, whereby the polymer comprises a percentage hydrophobic modification and a hydrophobic side chain comprising alkyl functional groups having a length. Without intending to be limited by theory, it is believed that the acidic monomers contribute to the ability of the polymer to swell in water upon neutralization of the acidic groups; and associative monomers anchor the polymer into structured surfactant hydrophobic domains, e.g., lamellae, to confer structure to the surfactant compositions and keep the polymer from collapsing and losing effectiveness in the presence of electrolyte. The crosslinked, associative polymer comprises a percentage hydrophobic modification, which is the mole percentage of monomers expressed as a percentage of the total number of all monomers in the polymer backbone, including both acidic and other non-acidic monomers. The percentage hydrophobic modification of the polymer, hereafter % HM, can be determined by the ratio of monomers added during synthesis, or by analytical techniques such as proton nuclear magnetic resonance (NMR). The alkyl side chain length can be determined similarly. Monomers comprising only 2 or fewer alkyl hydrocarbons (e.g., ethyl, methyl) are not considered associative for the purposes of the present invention, all side chains having more than 2 carbons being associative. Associative alkyl side chains comprise for example butyl, propyl, stearyl, steareth, cetyl, lauryl, laureth, octyl, behenyl, beheneth, steareth, or other linear, branched, saturated or unsaturated alkyl or alketh hydrocarbon side chains.

It has been discovered that crosslinked, associative polymers having preferred % HM and preferred carbon numbers of the hydrophobic end groups of the alkyl side chains provide significant enhancement of structure to structured surfactant compositions of the present invention, especially to inventive compositions comprising reduced levels of surfactant; and provide said structure at surprisingly low levels of polymer structurant. Concentrations of associative polymer of up to 5% or even 10% are taught in the art to obtain a sufficient amount structure, for example the exemplary compositions of U.S. Pat. No. 7,119,059 (Librizzi, et al) and U.S. Pat. No. 6,897,253 (Schmucker-Castner, et al). Inventors have found when the associative polymer % HM and the alkyl side chain number of carbons is optimized, structure of the aqueous structured surfactant phase is increased using only less than 3 wt % associative polymer as a percentage of the aqueous structured surfactant phase, preferably less than 2%, more preferably less than 1%, and even only about 0.2% of the phase, as demonstrated by the inventive examples hereinbelow.

The acidic monomer can comprise any acid functional group, for example sulfate, sulfonate, carboxylate, phosphonate, or phosphate or mixtures of acid groups. In one embodiment, the acidic monomer comprises a carboxylate, alternatively the acidic monomer is an acrylate, including acrylic acid and/or methacrylic acid. The acidic monomer comprises a polymerizable structure, e.g., vinyl functionality. Mixtures of acidic monomers, for example acrylic acid and methacrylic acid monomer mixtures, are useful.

The associative monomer comprises a hydrophobic end group and a polymerizable component, e.g., vinyl, which are attached. The hydrophobic end group can be attached to the polymerizable component, hence to the polymer chain, by different means but preferably is attached by an ether or ester or amide functionality, such as an alkyl acrylate or a vinyl alkanoate monomer. The hydrophobic end group can also be separated from the chain, for example by an alkoxy ligand such as an alkyl ether. In one embodiment, the associative monomer is an alkyl ester, alternatively an alkyl(meth)acrylate, where (meth)acrylate is understood to mean either methyl acrylate or acrylate or mixtures of the two.

In one embodiment, the hydrophobic end group of the associative polymer is incompatible with the aqueous phase of the composition and associates with the lathering surfactant hydrophobe components of the current invention. Without intending to be limited by theory, it is believed that the longer alkyl chains of the structuring polymer hydrophobe end groups increase incompatibility with the aqueous phase to enhance structure, whereas somewhat shorter alkyl chains having carbon numbers closely resembling lathering surfactant hydrophobes (e.g., 12 to 14 carbons) or multiples thereof (for bilayers, e.g.) are also effective, so a range of preferred materials balancing these opposing requirements, limited by solubility of the total molecule itself, is ideal. Polymers having short alkyl side chains, e.g., less than 6 carbons, are ineffective for the present invention. Inventors have discovered an ideal range of hydrophobic end group carbon numbers combined with an optimal percentage of hydrophobic monomers expressed as a percentage of the polymer backbone provides increased structure to the lathering, structured surfactant composition at low levels of polymer structurant.

Preferred associative polymers comprise about C16 (cetyl) alkyl hydrophobic side chains with about 0.7% hydrophobic modification, but the percentage hydrophobic modification can be up to the aqueous solubility limit in surfactant compositions, e.g., up to 2% or 5% or 10%. An exemplary preferred associative polymer is Aqupec SER-300 made by Sumitomo Seika of Japan, which is Acrylates/C10-30 alkyl acrylate crosspolymer and comprises stearyl side chains with less than about 1% HM. Other preferred associative polymers comprise stearyl, octyl, decyl and lauryl side chains. Preferred associative polymers are Aqupec SER-150 (acrylates/C10-30 alkyl acrylates crosspolymer) comprising about C18 (stearyl) side chains and about 0.4% HM, and Aqupec HV-701EDR which comprises about C8 (octyl) side chains and about 3.5% HM. Another preferred polymer is Stabylen 30 manufactured by 3V Sigma S.p.A., which has branched isodecanoate hydrophobic associative side chains. Importantly, inventors have discovered not all crosslinked, associative polymers are effective, and many are deleterious to structure. Associative polymers having hydrophobe side chains with fewer than 7 carbons and having % HM greater than about 25% or about 50% are dispreferred. For example, Carbopol Aqua SF-1 (crosslinked acrylates copolymer) having average 4.5 carbon alkyl side chains and more than 50% HM is deleterious to structure as demonstrated by the examples hereinbelow.

Deposition Polymers

The personal care compositions of the present invention can additionally comprise an organic cationic deposition polymer in the one or more phases as a deposition aid for the benefit agents described herein. Suitable cationic deposition polymers for use in the compositions of the present invention contain cationic nitrogen-containing moieties such as quaternary ammonium moieties. Nonlimiting examples of cationic deposition polymers for use in the personal cleansing composition include polysaccharide polymers, such as cationic cellulose derivatives. Preferred cationic cellulose polymers are the salts of hydroxyethyl cellulose reacted with trimethyl ammonium substituted epoxide, referred to in the industry (CTFA) as Polyquaternium 10 which are available from Amerchol Corp. (Edison, N.J., USA) in their Polymer KG, JR and LR series of polymers with the most preferred being KG-30M. Other suitable cationic deposition polymers include cationic guar gum derivatives, such as guar hydroxypropyltrimonium chloride, specific examples of which include the Jaguar series (preferably Jaguar C-17) commercially available from Rhodia Inc., and N-Hance polymer series commercially available from Aqualon.

In one embodiment, the deposition polymers of the present invention have a cationic charge density from about 0.8 meq/g to about 2.0 meq/g, alternatively from about 1.0 meq/g to about 1.5 meq/g.

Water

The surfactant phase of the present invention also comprises water. In one embodiment, the surfactant phase of the personal care composition comprises from about 10% to about 90%, alternatively from about 40% to about 85%, alternatively from about 60% to about 80% by weight water.

Benefit Phase

The personal care compositions of the present invention comprise a benefit phase. The benefit phase in the present invention is preferably hydrophobic or essentially anhydrous and can be substantially free of water. The benefit phase can be substantially free or free of surfactant.

The benefit phase typically comprises benefit agents. Benefit agents include water insoluble or hydrophobic benefit agents. The benefit phase may comprise from about 0.1% to about 50%, preferably from about 1% to about 30%, more preferably from about 5% to about 30%, by weight of the personal care composition, of a benefit agent.

The hydrophobic skin benefit agent for use in the benefit phase of the composition has a Vaughan Solubility Parameter (VSP) of from about 5 to about 15, preferably from about 5 to less than 10. These solubility parameters are well known in the formulation arts, and are defined by Vaughan in Cosmetics and Toiletries, Vol. 103, p 47-69, October 1988.

Non-limiting examples glycerides suitable for use as hydrophobic skin benefit agents herein include castor oil, soy bean oil, derivatized soybean oils such as maleated soy bean oil, safflower oil, cotton seed oil, corn oil, walnut oil, peanut oil, olive oil, cod liver oil, almond oil, avocado oil, palm oil and sesame oil, vegetable oils, sunflower seed oil, and vegetable oil derivatives; coconut oil and derivatized coconut oil, cottonseed oil and derivatized cottonseed oil, jojoba oil, cocoa butter, and combinations thereof.

Non-limiting examples of acetoglyceride esters suitable for use as hydrophobic skin benefit agents herein include acetylated monoglycerides.

Non-limiting examples of alkyl esters suitable for use as hydrophobic skin benefit agents herein include isopropyl esters of fatty acids and long chain esters of long chain (i.e. C10-C24) fatty acids, e.g. cetyl ricinoleate, non-limiting examples of which include isopropyl palmitate, isopropyl myristate, cetyl riconoleate and stearyl riconoleate. Other examples are: hexyl laurate, isohexyl laurate, myristyl myristate, isohexyl palmitate, decyl oleate, isodecyl oleate, hexadecyl stearate, decyl stearate, isopropyl isostearate, diisopropyl adipate, diisohexyl adipate, dihexyldecyl adipate, diisopropyl sebacate, acyl isononanoate lauryl lactate, myristyl lactate, cetyl lactate, and combinations thereof.

Non-limiting examples of alkenyl esters suitable for use as hydrophobic skin benefit agents herein include oleyl myristate, oleyl stearate, oleyl oleate, and combinations thereof.

Non-limiting examples of polyglycerin fatty acid esters suitable for use as hydrophobic skin benefit agents herein include decaglyceryl distearate, decaglyceryl diisostearate, decaglyceryl monomyriate, decaglyceryl monolaurate, hexaglyceryl monooleate, and combinations thereof.

Non-limiting examples of lanolin and lanolin derivatives suitable for use as hydrophobic skin benefit agents herein include lanolin, lanolin oil, lanolin wax, lanolin alcohols, lanolin fatty acids, isopropyl lanolate, acetylated lanolin, acetylated lanolin alcohols, lanolin alcohol linoleate, lanolin alcohol riconoleate, and combinations thereof.

Non-limiting examples of silicone oils suitable for use as hydrophobic skin benefit agents herein include dimethicone copolyol, dimethylpolysiloxane, diethylpolysiloxane, mixed C1-C30 alkyl polysiloxanes, phenyl dimethicone, dimethiconol, and combinations thereof. Preferred are non-volatile silicones selected from dimethicone, dimethiconol, mixed C1-C30 alkyl polysiloxane, and combinations thereof. Non-limiting examples of silicone oils useful herein are described in U.S. Pat. No. 5,011,681 (Ciotti et al.).

Still other suitable hydrophobic skin benefit agents include milk triglycerides (e.g., hydroxylated milk glyceride) and polyol fatty acid polyesters.

Still other suitable hydrophobic skin benefit agents include wax esters, non-limiting examples of which include beeswax and beeswax derivatives, spermaceti, myristyl myristate, stearyl stearate, and combinations thereof. Also useful are vegetable waxes such as carnauba and candelilla waxes; sterols such as cholesterol, cholesterol fatty acid esters; and phospholipids such as lecithin and derivatives, sphingo lipids, ceramides, glycosphingo lipids, and combinations thereof. Also suitable benefit agents include glycerol monooleate.

Skin Actives and Solid Particles

The compositions may optionally comprise the following skin benefit ingredients for enhanced delivery of these benefit materials on skin.

A) Desquamation Actives

Desquamation actives enhance the skin appearance benefits of the present invention. For example, the desquamation actives tend to improve the texture of the skin (e.g., smoothness). One desquamation system that is suitable for use herein contains sulfhydryl compounds and zwitterionic surfactants and is described in U.S. Pat. No. 5,681,852, to Bissett. Preferred concentrations of desquamation actives range from about 0.1% to about 10%, more preferably from about 0.2% to about 5%, even more preferably from about 0.5% to about 4%, by weight of the personal cleansing composition.

Another desquamation system that is suitable for use herein contains salicylic acid and zwitterionic surfactants and is described in U.S. Pat. No. 5,652,228 to Bissett. Zwitterionic surfactants such as described in these applications are also useful as desquamatory agents herein, with cetyl betaine being particularly preferred.

B) Anti-Wrinkle Actives/Anti-Atrophy Actives

Anti-wrinkle actives or anti-atrophy actives include sulfur-containing D and L amino acids and their derivatives and salts, particularly the N-acetyl derivatives. A preferred example of which is N-acetyl-L-cysteine; thiols, e.g. ethane thiol; hydroxy acids (e.g., alpha-hydroxy acids such as lactic acid and glycolic acid or beta-hydroxy acids such as salicylic acid and salicylic acid derivatives such as the octanoyl derivative), phytic acid, lipoic acid; lysophosphatidic acid, and skin peel agents (e.g., phenol and the like).

Hydroxy acids as skin active agents herein include salicylic acid and salicylic acid derivatives, preferred concentrations of anti-wrinkle/anti-atrophy actives range from about 0.01% to about 50%, more preferably from about 0.1% to about 10%, even more preferably from about 0.5% to about 2%, by weight of the personal cleansing composition.

Other non-limiting examples of suitable anti-wrinkle actives for use herein are described in U.S. Pat. No. 6,217,888, issued to Oblong et al.

C) Anti-Oxidants/Radical Scavengers

Non-limiting examples of anti-oxidants or radical scavengers for use herein include ascorbic acid and its salts, ascorbyl esters of fatty acids, ascorbic acid derivatives (e.g., magnesium ascorbyl phosphate, sodium ascorbyl phosphate, ascorbyl sorbate), tocopherol, tocopherol acetate, other esters of tocopherol, butylated hydroxy benzoic acids and their salts, 6-hydroxy-2,5,7,8-tetramethylchroman-2-carboxylic acid (commercially available under the tradename Trolox®), gallic acid and its alkyl esters, especially propyl gallate, uric acid and its salts and alkyl esters, sorbic acid and its salts, lipoic acid, amines (e.g., N,N-diethylhydroxylamine, amino-guanidine), sulfhydryl compounds (e.g., glutathione), dihydroxy fumaric acid and its salts, lycine pidolate, arginine pilolate, nordihydroguaiaretic acid, bioflavonoids, curcumin, lysine, methionine, proline, superoxide dismutase, silymarin, tea extracts, grape skin/seed extracts, melanin, and rosemary extracts may be used. The preferred concentrations range from about 0.1% to about 10%, more preferably from about 1% to about 5%, by weight of the personal cleansing composition.

D) Chelators

The term "chelating agent" or "chelator" refers to those skin active agents capable of removing a metal ion from a system by forming a complex so that the metal ion cannot readily participate in or catalyze chemical reactions.

The chelating agents as skin active agents for use herein are preferably included at concentrations ranging from about 0.1% to about 10%, more preferably from about 1% to about 5%, by weight of the personal cleansing composition. Non-limiting examples of suitable chelating agents are described in U.S. Pat. No. 5,487,884, issued Jan. 30, 1996 to Bissett et al.; International Publication No. 91/16035, Bush et al., published Oct. 31, 1995; and International Publication No. 91/16034, Bush et al., published Oct. 31, 1995.

A preferred chelating agent for use in the compositions of the present invention includes disodium EDTA, and derivatives thereof.

E) Anti-Cellulite Agents

Non-limiting examples of anti-cellulite agents include xanthine compounds such as caffeine, theophylline, theobromine, aminophylline, and combinations thereof. Anti-cellulite agents are preferably included at concentrations ranging from about 0.1% to about 10%, more preferably from about 1% to about 5%, by weight of the personal cleansing composition.

F) Tanning Actives

Non-limiting examples of such tanning agents include dihydroxyacetone, which is also known as DHA or 1,3-dihydroxy-2-propanone. Tanning actives are preferably included at concentrations ranging from about 0.1% to about 10%, more preferably from about 1% to about 5%, by weight of the personal cleansing composition.

G) Skin Lightening Agents

Non-limiting examples of skin lightening agents suitable for use herein include kojic acid, arbutin, ascorbic acid and derivatives thereof (e.g., magnesium ascorbyl phosphate or sodium ascorbyl phosphate), and extracts (e.g., mulberry extract, placental extract). Non-limiting examples of skin lightening agents suitable for use herein also include those described in WO 95/34280, WO 95/07432, and WO 95/23780. Skin lightening agents are preferably included at concentrations ranging from about 0.1% to about 10%, more preferably from about 1% to about 5%, by weight of the personal cleansing composition.

H) Skin Soothing and Skin Healing Actives

Non-limiting examples of skin soothing or skin healing actives suitable for use herein include panthenoic acid derivatives (e.g., panthenol, dexpanthenol, ethyl panthenol), aloe vera, allantoin, bisabolol, and dipotassium glycyrrhizinate. Skin soothing and skin healing actives are preferably included at concentrations ranging from about 0.1% to about 10%, more preferably from about 1% to about 5%, by weight of the personal cleansing composition.

I) Antimicrobial Actives

Non-limiting examples of antimicrobial actives for use herein includes β-lactam drugs, quinolone drugs, ciprofloxacin, norfloxacin, tetracycline, erythromycin, amikacin, 2,4,4'-trichloro-2'-hydroxy diphenyl ether, 3,4,4'-trichlorobanilide, phenoxyethanol, phenoxy propanol, phenoxyisopropanol, doxycycline, capreomycin, chlorhexidine, chlortetracycline, oxytetracycline, clindamycin, ethambutol, hexamidine isethionate, metronidazole, pentamidine, gentamicin, kanamycin, lineomycin, methacycline, methenamine, minocycline, neomycin, netilmicin, paromomycin, streptomycin, tobramycin, miconazole, tetracycline hydrochloride, erythromycin, zinc erythromycin, erythromycin estolate, erythromycin stearate, amikacin sulfate, doxycycline hydrochloride, capreomycin sulfate, chlorhexidine gluconate, chlorhexidine hydrochloride, chlortetracycline hydrochloride, oxytetracycline hydrochloride, clindamycin hydrochloride, ethambutol hydrochloride, metronidazole hydrochloride, pentamidine hydrochloride, gentamicin sulfate, kanamycin sulfate, lineomycin hydrochloride, methacycline hydrochloride, methenamine hippurate, methenamine mandelate, minocycline hydrochloride, neomycin sulfate, netilmicin sulfate, paromomycin sulfate, streptomycin sulfate, tobramycin sulfate, miconazole hydrochloride, ketaconazole, amanfadine hydrochloride, amanfadine sulfate, octopirox, parachlorometa xylenol, nystatin, tolnaftate, zinc pyrithione, clotrimazole, and combinations thereof.

Antimicrobials are preferably included at concentrations ranging from about 0.1% to about 10%, more preferably from about 1% to about 5%, by weight of the personal cleansing composition.

J) Sunscreen Actives

Non-limiting examples of sunscreen actives, either organic or inorganic for use herein are described below. Among the inorganic sunscreens useful herein are metallic oxides such as titanium dioxide having an average primary particle size of from about 15 nm to about 100 nm, zinc oxide having an average primary particle size of from about 15 nm to about 150 nm, zirconium oxide having an average primary particle size of from about 15 nm to about 150 nm, iron oxide having an average primary particle size of from about 15 nm to about 500 nm, and mixtures thereof.

The concentration of the sunscreen active for use in the composition preferably ranges from about 0.1% to about 20%, more typically from about 0.5% to about 10%, by weight of the composition. Exact amounts of such sunscreen actives will vary depending upon the sunscreen or sunscreens chosen and the desired Sun Protection Factor (SPF).

A wide variety of conventional organic sunscreen actives are also suitable for use herein, non-limiting examples of which include p-aminobenzoic acid, its salts and its derivatives (ethyl, isobutyl, glyceryl esters; p-dimethylaminobenzoic acid); anthranilates (i.e., o-amino-benzoates; methyl, menthyl, phenyl, benzyl, phenylethyl, linalyl, terpinyl, and cyclohexenyl esters); salicylates (amyl, phenyl, octyl, benzyl, menthyl, glyceryl, and di-pro-pyleneglycol esters); cinnamic acid derivatives (menthyl and benzyl esters, a-phenyl cinnamonitrile; butyl cinnamoyl pyruvate); dihydroxycinnamic acid derivatives (umbelliferone, methylumbelliferone, methylaceto-umbelliferone); trihydroxy-cinnamic acid derivatives (esculetin, methylesculetin, daphnetin, and the glucosides, esculin and daphnin); hydrocarbons (diphenylbutadiene, stilbene); dibenzalacetone and benzalacetophenone; naphtholsulfonates (sodium salts of 2-naphthol-3,6-disulfonic and of 2-naphthol-6,8-disulfonic acids); di-hydroxynaphthoic acid and its salts; o- and p-hydroxybiphenyldisulfonates; coumarin derivatives (7-hydroxy, 7-methyl, 3-phenyl); diazoles (2-acetyl-3-bromoindazole, phenyl benzoxazole, methyl naphthoxazole, various aryl benzothiazoles); quinine salts (bisulfate, sulfate, chloride, oleate, and tannate); quinoline derivatives (8-hydroxyquinoline salts, 2-phenylquinoline); hydroxy- or methoxy-substituted benzophenones; uric and violuric acids; tannic acid and its derivatives (e.g., hexaethylether); (butyl carbotol) (6-propyl piperonyl)ether; hydroquinone; benzophenones (oxybenzene, sulisobenzone, dioxybenzone, benzoresorcinol, 2,2',4,4'-tetrahydroxybenzophenone, 2,2'-dihydroxy-4,4'-dimethoxybenzophenone, octabenzone; 4-isopropyldibenzoylmethane; butylmethoxydibenzoylmethane; etocrylene; octocrylene; [3-(4'-methylbenzylidene bornan-2-one), terephthalylidene dicamphor sulfonic acid and 4-isopropyl-di-benzoylmethane. Among these sunscreens, preferred are 2-ethylhexyl-p-methoxycinnamate (commercially available as PARSOL MCX), 4,4'-t-butyl methoxydibenzoyl-methane (commercially available as PARSOL 1789), 2-hydroxy-4-methoxybenzophenone, octyldimethyl-p-aminobenzoic acid, digalloyltrioleate, 2,2-dihydroxy-4-methoxybenzophenone, ethyl-4-(bis(hydroxypropyl))aminobenzoate, 2-ethylhexyl-2-cyano-3,3-diphenylacrylate, 2-ethylhexyl-salicylate, glyceryl-p-aminobenzoate, 3,3,5-tri-methylcyclohexylsalicylate, methylanthranilate, p-dimethyl-aminobenzoic acid or aminobenzoate, 2-ethylhexyl-p-dimethyl-amino-benzoate, 2-phenylbenzimidazole-5-sulfonic acid, 2-(p-dimethylaminophenyl)-5-sulfonicbenzoxazoic acid, octocrylene and combinations thereof.

K) Solid Particulates

The compositions of the present invention may comprise a solid particle. Nonlimiting examples of the solid particles include: interference pigment, multi-layered pigment, metallic particle, solid and liquid crystals, or combinations thereof. An interference pigment is a pigment with pearl gloss prepared by coating the surface of a particle substrate material with a thin film. The particle substrate material is generally platelet in shape. The thin film is a transparent or semitransparent material having a high refractive index. The high refractive index material shows a pearl gloss resulting from mutual interfering action between reflection and incident light from the platelet substrate/coating layer interface and reflection of incident light from the surface of the coating layer. The interference pigments of the multi-phased personal care compositions preferably comprises no more than about 20 weight percent of the composition, more preferably no more than about 10 weight percent, even more preferably no more than about 7 weight percent, and still more preferably no more than about 5 weight percent of the multi-phased personal care composition. The interference pigment of the multi-phased personal care composition preferably comprises at least about 0.1 weight percent of the multi-phased personal care composition, more preferably at least about 0.2 weight percent, even more preferably at least about 0.5 weight percent, and still more preferably at least about 1 weight percent by weight of the composition. When pigment is applied and rinsed as described in the Pigment Deposition Tape Strip Method as described in copending application Ser. No. 60/469,075 filed on May 8, 2003, the deposited pigment on the skin is preferably at least 0.5 µg/cm2, more preferably at least 1 µg/cm2, and even more preferably at least 5 µg/cm2. In an embodiment of the present invention the interference pigment surface is either hydrophobic or has been hydrophobically modified. The Particle Contact Angle Test as described in application Ser. No. 60/469,075 filed on May 8, 2003 is used to determine contact angle of interference pigments. The greater the contact angle, the greater the hydrophobicity of the interference pigment. The interference pigment of the present invention possess a contact angle of at least 60 degrees, more preferably greater than 80 degrees, even more preferably greater than 100 degrees, still more preferably greater than 100 degrees. The hydrophobically modified interference pigment or HMIP allows for the entrapment of the HMIP within the phases and greater deposition of the HMIP. Preferably the ratio of HMIP to a phase is 1:1 to about 1:70, more preferably 1:2 to about 1:50, still more preferably 1:3 to about 1:40 and most preferably 1:7 to about 1:35.

In an embodiment of the present invention the HMIP's are preferably entrapped within the benefit phase. This necessitates that the benefit phase particle size is generally larger than the HMIP. In a preferred embodiment of the invention, the benefit phase particles contain only a small number of HMIPs per benefit particles. Preferably this is less than 20, more preferably less than 10, most preferably less than 5. These parameters, the relative size of the benefit droplets to the HMIP and the approximate number of HMIP particles per benefit particles, can be determined by using visual inspection with light microscopy.

The HMIP and the benefit phase can be mixed into the composition via a premix or separately. For the case of separate addition, the hydrophobic pigments partition into the benefit phase during the processing of the formulation. The HMIP of the present invention preferably has a hydrophobic coating comprising no more than about 20 weight percent of the total particle weight, more preferably no more than about 15 weight percent, even more preferably no more than about 10 weight percent. The HMIP of the present invention preferably has a hydrophobic coating comprising at least about 0.1 weight percent of the total particle weight, more preferably at least about 0.5 weight percent, even more preferably at least about 1 weight percent. Nonlimiting examples of the hydrophobic surface treatment useful herein include silicones, acrylate silicone copolymers, acrylate polymers, alkyl silane, isopropyl titanium triisostearate, sodium stearate, magnesium myristate, perfluoroalcohol phosphate, perfluoropolymethyl isopropyl ether, lecithin, carnauba wax, polyethylene, chitosan, lauroyl lysine, plant lipid extracts and mixtures thereof, preferably, silicones, silanes and stearates. Surface treatment houses include US Cosmetics, KOBO Products Inc., and Cardre Inc.

L) Anti-Dandruff Agents

The shampoo compositions of the present invention may also contain an anti-dandruff agent. Suitable, non-limiting examples of anti-dandruff agents include: pyridinethione salts, specifically the zinc salt of 1-hydroxy-2-pyridinethione (known as "zinc pyridinethione" or "ZPT"), azoles, selenium sulfide, particulate sulfur, keratolytic acid, salicylic acid, octopirox (piroctone olamine), coal tar, and combinations thereof. In one aspect, the anti-dandruff agents typically are pyridinethione salts. Such anti-dandruff agents should be physically and chemically compatible with the essential components of the composition, and should not otherwise unduly impair product stability, aesthetics or performance.

Pyridinethione anti-dandruff agents are described, for example, in U.S. Pat. No. 2,809,971; U.S. Pat. No. 3,236,733; U.S. Pat. No. 3,753,196; U.S. Pat. No. 3,761,418; U.S. Pat. No. 4,345,080; U.S. Pat. No. 4,323,683; U.S. Pat. No. 4,379,753; and U.S. Pat. No. 4,470,982. It is contemplated that when ZPT is used as the anti-dandruff particulate in the compositions herein, that the growth or re-growth of hair may be stimulated or regulated, or both, or that hair loss may be reduced or inhibited, or that hair may appear thicker or fuller.

Optional Ingredients

While not essential for the purposes of the present invention, the non-limiting list of materials, in addition to the previously disclosed, optional materials, illustrated hereinafter are suitable for use in the personal care composition, and may be desirably incorporated in certain embodiments, for example to assist or enhance cleansing performance, for treatment of the skin, or to modify the aesthetics of the personal care composition as is the case with perfumes, colorants, dyes or the like. Optional materials useful in the products herein are categorized or described by their cosmetic and/or therapeutic benefit or their postulated mode of action or function. However, it is to be understood that the active and other materials useful herein can, in some instances, provide more than one cosmetic and/or therapeutic benefit or function or operate via more than one mode of action. Therefore, classifications herein are made for the sake of convenience and are not intended to limit an ingredient to the particularly stated application or applications listed. The precise nature of these optional materials, and levels of incorporation thereof, will depend on the physical form of the composition and the nature of the cleansing operation for which it is to be used. The optional materials are usually formulated at less than about less than about 6%, less than about 5%, less than about 4%, less than about 3%, less than about 2%, less than about 1%, less than about 0.5%, less than about 0.25%, less than about 0.1%, less than about 0.01%, less than about 0.005% of the personal care composition.

To further improve stability under stressful conditions such as high temperature and vibration, it is preferable to adjust the densities of the separate phases such that they are substantially equal. To achieve this, low density microspheres can be added to one or more phases of the personal care composition, preferably the structured surfactant phase. Personal care composition that comprises low density microspheres are described in a patent application published on May 13, 2004 under U.S. Patent Publication No. 2004/0092415A1 entitled "Striped Liquid Personal Cleansing Compositions Containing A Cleansing Phase and A Separate Phase with Improved Stability," filed on Oct. 31, 2003 by Focht, et al.

Other non limiting optional ingredients that can be used in the personal care composition of the present invention can comprise an optional benefit component that is selected from the group consisting of thickening agents; preservatives; antimicrobials; fragrances; chelators (e.g. such as those described in U.S. Pat. No. 5,487,884 issued to Bisset, et al.); sequestrants; vitamins (e.g. Retinol); vitamin derivatives (e.g. tocophenyl actetate, niacinamide, panthenol); sunscreens; desquamation actives (e.g. such as those described in U.S. Pat. Nos. 5,681,852 and 5,652,228 issued to Bisset); anti-wrinkle/anti-atrophy actives (e.g. N-acetyl derivatives, thiols, hydroxyl acids, phenol); anti-oxidants (e.g. ascorbic acid derivatives, tocophenol) skin soothing agents/skin healing agents (e.g. panthenoic acid derivatives, aloe vera, allantoin); skin lightening agents (e.g. kojic acid, arbutin, ascorbic acid derivatives) skin tanning agents (e.g. dihydroxyacteone); anti-acne medicaments; essential oils; sensates; pigments; colorants; pearlescent agents; interference pigments (e.g such as those disclosed in U.S. Pat. No. 6,395,691 issued to Liang Sheng Tsaur, U.S. Pat. No. 6,645,511 issued to Aronson, et al., U.S. Pat. No. 6,759,376 issued to Zhang, et al, U.S. Pat. No. 6,780,826 issued to Zhang, et al.) particles (e.g. talc, kolin, mica, smectite clay, cellulose powder, polysiloxane, silicas, carbonates, titanium dioxide, polyethylene beads) hydrophobically modified non-platelet particles (e.g. hydrophobically modified titanium dioxide and other materials described in a commonly owned, patent application published on Aug. 17, 2006 under Publication No. 2006/0182699A, entitled "Personal Care Compositions Containing Hydrophobically Modified Non-platelet particle filed on Feb. 15, 2005 by Taylor, et al.) and mixtures thereof. In one aspect, the multiphase personal care composition may comprise from about 0.1% to about 4%, by weight of the multiphase personal care composition, of hydrophobically modified titanium dioxide.

Other optional ingredients are most typically those materials approved for use in cosmetics and that are described in the CTFA Cosmetic Ingredient Handbook, Second Edition, The Cosmetic, Toiletries, and Fragrance Association, Inc. 1988, 1992.

Test Methods

The current invention utilizes a number of test methods to determine various metrics of structure. The methodology for these tests and associated examples are illustrated below.

Determining Degree of Complexation.

The degree of complexation for each PRM=[Total fragrance in BCD-free fragrance]/[Total fragrance]*100%

Determining the Total Fragrance in BCD 1 g of sample was placed in a 125 ml square bottle with 50 mls (39.25 g) acetone, sample heated at 70 C for 5 hours and then shaken for 1 hour prior to filtering and injection. Analyzed using gas chromatography—mass spectroscopy.

Diphenyl oxide was used as internal standard (800 mg in 1 liter of acetone).

Determining the Uncomplexed Fragrance in BCD 0.2 g of sample was placed in a 20 ml vial, extract with 10 mls of THF gently for 10 inversions.

Determining the Degree of BCD-PRM Complex Retention in Neat Body Wash Product

BCD-PRM complex is prepared where the degree of complexation is greater than 90%.

Control product: Body wash with a free fragrance

Test product: Same body wash with equivalent total fragrance all coming from BCD-PRM complex Degree of complex retention is determined by the average ratio of the headspace concentration of all PRMs above the test product over the control product.

If the ratio is one, the degree of complex retention is zero as all PRMs are released from the BCD and the test body wash product behaves the same as the control product.

If the ratio is zero, the degree of complex retention is one as all PRMs are complexed with the BCD, there are no PRMs released from the product.

Solid-Phase Micro-Extraction (SPME)-Gas Chromatography/Mass Spectrometry ("GC-MS") was used to measure the relative level of perfume raw materials in the headspace of products. 1.0 grams of the control and test product are placed into clean 20 ml headspace vials and allowed to equilibrate for at least 2 hours at room temperature.

The samples are then analyzed using the MPS2-SMPE-GC-MS analysis system (GC-02001-0153, MSD-02001-0154, MPS2-02001-0155).

Apparatus:
1. 20 ml headspace vial
2. Timer.
3. Gas Chromatograph (GC): Agilent model 6890 with a CIS-4 injector (Gerstel, Mulheim, Germany) and MPS-2 Autosampler and TDU. For SPME analysis, we used the split/splitless injector (not the CIS-4 injector).
4. GC column: J&W DB-5 MS, 30 M×0.25 mm ID, 1.0 □m film thickness obtained from J&W Scientific of Folsom, Calif., USA.
5. Carrier gas, helium, 1.5 ml/min. flow rate.
6. The injector liner is a special SPME liner (0.75 mm ID) from Supelco.
7. The Detector is a model 5973 Mass Selective Detector obtained from Agilent Technologies, Inc., Wilmington, Del., USA having a source temperature of about 230° C., and a MS Quad temperature of about 150° C.

Analysis Procedure:
1. Transfer sample to proper sample tray and proceed with SPME-GC-MS analysis.
2. Start sequence of sample loading and analysis. In this step, the sample is allowed to equilibrate for at least two hours on the auto sampler tray, then sampled directly from the tray. The SPME fiber assembly is DVB/CAR/PDMS (50/30 um, 24 ga, 1 cm length). Sampling time is 5 minutes.
3. Injector temperature is at 260 C.
4. Then GC-MS analysis run is started. Desportion time is 5 minutes.
5. The following temperature program is used:
    i) an initial temperature of about 50° C. which is held for 3 minutes,
    ii) increase the initial temperature at a rate of about 6° C./min until a temperature of about 250° C. is reached, then 25° C./min to 275° C., hold at about 275° C. for 4.67 minute.
6. Perfume compounds are identified using the MS spectral libraries of John Wiley & Sons and the National Institute of Standards and Technology (NIST), purchased and licensed through Hewlett Packard.
7. Chromatographic peaks for specific ions are integrated using the Chemstation software obtained from Agilent Technologies, Inc., Wilmington, Del., USA.
8. The ratio for each PRM is taken as the ratio of the peak area for the perfume raw material in product A vs. product B
9. The average ratio is calculated as the average of the ratio obtained in step 8 for all perfume raw materials.

Determining the Average Ratio of Diluted Over Neat Headspace Concentration for all Perfume Products ("ARDON") Value Headspace GC-MS is used to measure the differences of perfumes in the diluted product (1:10 water dilution) headspace vs. in the neat headspace. Table 2 illustrates the results of ARDON testing.

2 Grams of Product in 20 mls HS Vial

TABLE 2

| | Sample description | BCD or BCD-Perfume | ARDON |
|---|---|---|---|
| 1 | Body Wash Chassis with BCD complex | Yes | 179% ± 25% |
| 2 | Body Wash Chassis with free perfume | No | 117% ± 12% |
| 3 | Commercially available Body Wash 1* Irish Spring Body Wash | No | 102% |
| 4 | Commercially available Body Wash 2** Dial Body Wash | No | 86% |

Zero Shear Viscosity and Young's Modulus Methods

The Zero Shear Viscosity of a material which is a phase or a composition of the present composition, can be measured either prior to combining in the composition, after preparing a composition, or first separating a phase or component from a composition by suitable physical separation means, such as centrifugation, pipetting, cutting away mechanically, rinsing, filtering, or other separation means.

A controlled stress rheometer such as a TA Instruments AR2000Rheometer is used to determine the Zero Shear Viscosity. The determination is performed at 25° C. with the 4 cm diameter parallel plate measuring system and a 1 mm gap. The geometry has a shear stress factor of 79580 m-3 to convert torque obtained to stress. Serrated plates can be used to obtain consistent results when slip occurs.

First the material is positioned on the rheometer base plate, the measurement geometry (upper plate) is moved into position 1.1 mm above the base plate. Excess material at the geometry edge is removed by scraping after locking the geometry. The geometry is then moved to the target 1 mm position above the base plate and a pause of about 2 minutes is allowed to allow loading stresses to relax. This loading procedure ensures no tangential stresses are loaded at the measurement onset, which can influence results obtained. If the material comprises particles discernible to the eye or by feel (beads, e.g.) which are larger than about 150 microns in number average diameter, the gap setting between the base plate and upper plate is increased to the smaller of 4 mm or 8-fold the diameter of the 95th volume percentile particle diameter. If a phase has any particle larger than 5 mm in any dimension, the particles are removed prior to the measurement.

The measurement is performed by applying a continuous shear stress ramp from 0.1 Pa to 1,000 Pa over a time interval of 4 minutes using a logarithmic progression, i.e., measurement points evenly spaced on a logarithmic scale. Thirty (30)

measurement points per decade of stress increase are obtained. If the measurement result is incomplete, for example if material is observed to flow from the gap, results obtained are evaluated with incomplete data points excluded. If there are insufficient points to obtain an accurate measurement, the measurement is repeated with increased number of sample points.

The Young's Modulus (Pa) is obtained by graphing the Stress (Pa) vs. Strain (unitless) and obtaining the slope of the regression line of the initial linear region between Stress vs. Strain, typically occurring in the region below about 4% strain. If the relationship is not linear, the linear regression line slope below 2% strain is taken as the Young's Modulus (Pa), using unitless strain.

The Zero Shear Viscosity is obtained by taking a first median value of viscosity in Pascal-seconds (Pa-sec) for viscosity data obtained between and including 0.1 Pa and the point where viscosity begins to steeply decline. After taking the first median viscosity, all viscosity values greater than 5-fold the first median value and less than 0.2× the median value are excluded, and a second median viscosity value is obtained of the same viscosity data, excluding the indicated data points. The second median viscosity so obtained is the Zero Shear Viscosity.

Compositions of the present invention have a Zero Shear Viscosity of at least about 100 Pa-s, alternatively at least about 300 Pa-s, alternatively at least about 500 Pa-s, alternatively at least about 1000 Pa-s, alternatively at least about 1500 Pa-s, alternatively at least about 2000 Pa-s.

Compositions of the present invention have a Young's Modulus of at least about 2 Pa, alternatively at least about 5 Pa, alternatively at least about 10 Pa, alternatively at least about 20 Pa, alternatively at least about 30 Pa, alternatively at least about 40 Pa, alternatively at least about 50 Pa, alternatively at least about 75 Pa.

Ultracentrifugation Method

The Ultracentrifugation Method is a physical method used to determine amount of structure in a composition or a subset of a composition. The method is also used to determine the rate at which a structured surfactant composition dissolves upon dilution to present effective amounts of surfactant to the cleaning environment proximal to surfaces.

A composition is separated by ultracentrifuge into separate but distinguishable layers. The multiphase personal care composition of the present invention can have multiple distinguishable layers (e.g., a structured surfactant layer, and a benefit layer).

First, dispense about 4 grams of composition into a Beckman Centrifuge Tube (11×60 mm) to fill the tube. Next, dilute the composition to a 10% Dilution Level using 90% of the composition and 10% DI water using an appropriate mixer and dispense the same amount of composition into a companion centrifuge tube. Continue to dilute the composition and fill tubes in the same manner until a 60% Dilution Level is obtained for the composition using 40% of the composition with 60% DI water. Place the centrifuge tubes in an ultracentrifuge (Beckman Model L8-M or equivalent) using a sling rotor and ultracentrifuge using the following conditions: 50,000 rpm, 2 hours, and 40° C.

Measure the relative phase volumes of the phases the composition by measuring the height of each layer using an Electronic Digital Caliper (within 0.01 mm) Layers are identified by those skilled in the art by physical observation techniques paired with chemical identification if needed. For example, the structured surfactant layer is identified by transmission electron microscopically (TEM), polarized light microscopy, and/or X-ray diffraction for the present invention as a structured lamellar phase comprising multilamellar vesicles, and the hydrophobic benefit layer is identified by its low moisture content (less than 10% water as measured by Karl Fischer Titration). The total height $H_a$ is measured which includes all materials in the ultracentrifuge tube. Next, the height of each layer is measured from the bottom of the centrifuge tube to the top of the layer, and the span of each layer algebraically determined by subtraction. The benefit layer may comprise several layers if the benefit phase has more than one component which may phase splits into liquid and waxy layers, or if there is more than one benefit component. If the benefit phase splits, the sum of the benefit layers measured is the benefit layer height, $H_b$. Generally, a hydrophobic benefit layer when present, is at the top of the centrifuge tube.

The surfactant phase may comprise several layers or a single layer, $H_c$. There may also be a micellar, unstructured, clear isotropic layer at the bottom or next to the bottom of the ultracentrifuge tube. The layers immediately above the isotropic phase generally comprise higher surfactant concentration with higher ordered structures (such as liquid crystals). These structured layers are sometimes opaque to naked eyes, or translucent, or clear. There may be several structured layers present, in which case $H_c$ is the sum of the individual structured layers. If any type of polymer-surfactant phase is present, it is considered a structured phase and included in the measurement of $H_c$. The sum of the aqueous phases is $H_s$.

Finally, the structured domain volume ratio is calculated as follows:

$$\text{Structured Domain Volume Ratio} = H_c/H_s * 100\%$$

If there is no benefit phase present, use the total height as the surfactant layer height, $H_s = H_a$. For the present invention, the Structured Domain Volume Ratio is the Lamellar Phase %. The measurement is made for each dilution prepared and centrifuged, i.e., the Structured Domain Volume Ratio is determined for the composition, and for 90%, 80%, 70% and 60% dilutions prepared as indicated above.

The highest amount of dilution (i.e., the lowest Dilution Level) wherein the composition maintains at least 95% Lamellar Phase % is an indicator of amount of structure for compositions having varying n values for STnS.

In one embodiment, the highest dilution wherein the composition has at least 95% lamellar phase is greater than about 15%, alternatively greater than about 25%, alternatively greater than about 35%.

In one embodiment, the composition has a Structured Domain Volume Ratio of at least about 40%, alternatively at least about 45%, alternatively at least about 50%, alternatively at least about 55%, alternatively at least about 60%, alternatively at least about 65%, alternatively at least about 70%, alternatively at least about 75%, alternatively at least about 80%, alternatively at least about 85%, and alternatively greater than about 90% by volume of the aqueous surfactant composition.

Ultracentrifugation Dilution Method

The Ultracentrifugation Dilution Method is a physical method used to determine amount of structure in a composition at a certain point in its dilution profile, which relates to the ability of the composition to lather. The Ultracentrifugation Dilution Method utilizes the results from the Ultracentrifugation Method at the 50% dilution point. When consumers use surfactant compositions with an implement such as a washcloth or a Puff, about 10 ml of composition is typically dosed onto the implement which can contain about 10 ml of water therein. Consumers agitate to generate lather, requiring the composition to rapidly dissolve at this dilution strength.

The ability of structured surfactant compositions to dissolve at 50% Dilution % is measured by the method.

The method is identical in all its details to the Ultracentrifugation Method. The result at 50% Dilution % is obtained for a composition and is expressed as the Diluted 50% Lamellar Phase Volume.

Results from the Ultracentrifugation Dilution Method parallel results obtained for the Dissolution Rate Test for the compositions of the current invention comprising STnS, affirming the relationship between high structure and reduced lather, and vice versa, leading to improved stability and use aesthetics within a narrower range of n values for STnS. The ST0S composition of Example 4 being relatively unstructured, has low structure upon dilution, but is unsuitable for the purposes of a structured surfactant composition due to its inability to provide requisite stabilization to a composition based on its rheology. The ST3S composition of Example 1 has sufficient structure and dilutes rapidly to micellar surfactants useful for lather and cleaning, but disadvantageously these ST3S compositions cannot readily be formulated into compositions comprising reduced surfactant levels; they will always remain costly, inefficient, environmentally less preferred, and less mild. The ST1S composition of Example 3 has a Diluted 50% Lamellar Phase Volume of 100%, which will result in poor lather and cleaning characteristics in many use modes. The ST2S composition of Example 2 demonstrates versatility in that it has a high degree of structure yet dilutes sufficiently to provide a good lather result, the lather performance supported by its Diluted 50% Lamellar Phase Volume value of 70%. ST2S compositions can be prepared at reduced surfactant levels, for example at 15%, or 12%, or 10% or 8% or even 6% surfactant and retain many of the preferred features of the present invention.

In one embodiment of the present invention, the Diluted 50% Lamellar Phase Volume for a composition of the present invention is less than about 90%, alternatively less than about 80%, alternatively less than 75%.

Dissolution Rate Method

Structured compositions are prone to slow dissolution, hence poor lather characteristics and cleaning can result. Slowly dissolving structured surfactant phases are largely behind the development of the "Puff" implement many years ago, an agitating implement that encourages dissolution, lather and cleaning. Lather and cleaning result from the ability of aqueous surfactant molecules to diffuse to and stabilize air interfaces and soil surfaces. When surfactants remain locked into lamellar or other organized structures, they are unable to diffuse in the aqueous phase and so must first dissolve as individual surfactant monomers and micelles in order to be effective. Dilution and agitation encourage dissolution during use. The Dissolution Rate Method measures the extent of dissolution of a surfactant composition in water.

A straight walled glass beaker is obtained having an inside diameter (i.d.) of 63 mm and an inside height of 87 mm, e.g. Pyrex 250 ml (No. 1000) which are widely available. 150 grams of distilled water at ambient temperature (75° F.) is poured into the beaker. A Teflon® coated magnetic stir bar is added to the beaker. The stir bar is nominally 1.5 inches long×5/16 inches diameter and octagonally shaped viewed from the end and has a 1/16 in. wide molded pivot ring around its center where the diameter is increased to about 0.35 in. Spinbar® magnetic stir bars are available from Sigma Aldrich Corp. worldwide including Milwaukee, Wis., USA and at www.sigmaaldrich.com.

Measure and record the Initial Water Conductivity of the water using a conductivity meter, e.g., a Mettler-Toledo SevenMulti meter with InLab740 probe, and record the value. The conductivity of the water should be about 2 microSemens/cm (uS/cm) or less to indicate a low level of dissolved solids present. Remove the conductivity probe from the water and place the beaker onto a digitally controlled laboratory stirrer, for example Ika® Werke RET Control-visc available, e.g., from DivTech Equipment Co, Cincinnati, Ohio, USA. The beaker is centered on the stirrer and the stirrer is turned on to obtain a constant rotation speed of 500 rpm, establishing a vortex in the water which measures about 3 cm depth from highest point of water at the beaker edge to lowest point of air at the vortex center. Observe the vortex from above to ensure it is centered in the beaker, and the magnetic stir bar centered at the vortex center.

Obtain a surfactant phase and fill it into a 1 ml syringe without entrapping air. The syringe has a diameter of about 1.9 mm at the tip (e.g., BD 1 ml tuberculin slip tip, Becton, Dickinson and Co., Franklin Lakes, N.J., USA). Inject the surfactant phase in a steady stream onto the top surface of the water near the beaker edge but not touching the beaker edge. The composition should be injected in about 1 second. Begin a timer and allow the composition to stir for 30 seconds.

Turn off the stirrer. Insert the conductivity probe into the water in a location away from any undissolved solids. Allow the measurement to stabilize and take a conductivity reading and record the Conductivity.

Turn the stirrer back on. Restart the timer as the digital readout passes 250 rpm. After an additional 30 seconds elapsed time, turn off the stirrer and measure the conductivity in the same manner as previous. Record the Conductivity.

Turn the stirrer back on. Restart the timer as the digital readout passes 250 rpm. After an additional 60 seconds elapsed time, turn off the stirrer and measure the conductivity in the same manner as previous. Record the Conductivity.

Remove the probe from the water without disturbing any remaining solids. Cap the beaker with a suitable watertight cover, e.g., plastic wrap and a rubber band. Shake the beaker vigorously for about 30 seconds to dissolve remaining solids, using a vortex type agitator in addition if necessary.

Uncap the beaker, measure conductivity and record the value as the Final Conductivity.

The Dissolution % at each time point is calculated according to the following equation:

$$\text{Dissolution \%} = 100\% \times (\text{Conductivity} - \text{Initial Water Conductivity})(\text{Final Conductivity} - \text{Initial Water Conductivity})$$

Repeat the measurement as needed to obtain a representative average value.

At the 60 second time point, compositions of the present invention have a Dissolution % of at least about 60%, alternatively at least about 70%, alternatively at least about 80%. At the 120 second time point, compositions of the present invention have a Dissolution % of at least about 80%, alternatively at least about 85%, alternatively at least about 90%, alternatively at least about 95%.

Third-Phase Method for Determining Structured Surfactant Stability

The "Third-Phase" Method is used to determine structured surfactant phase stability in a personal cleansing composition. The method involves placing the personal care compositions at 50° C. for 10 days for rapid aging. After rapid aging, transfer about 4 grams of the composition into a Beckman Centrifuge Tube (11×60 mm) Place the centrifuge tube in a Beckman LE-80 Ultracentrifuge and operate the Ultracentrifuge under the following conditions: 50,000 rpm, 2 hours, and @ 40 C.

After Ultracentrifugation, determine the third-phase volume by measuring the height of various surfactant phases using an Electronic Digital Caliper (within 0.01 mm).

The very top layer is hydrophobic benefit phase layer (hydrocarbons or soybean oil etc.). The layers below the hydrophobic benefit phase layers contain surfactant/water are determined in the following: $H_a$ is the height of all layers containing surfactant/water and $H_b$ is the height of the clear "third-phase" layer just below the hydrophobic benefit phase layer. It is important to record the readings within 30 mins after the Ultracentrifugation is finished to minimize material migration across different layers. The third phase volume is calculated as: Third-phase Volume %=$H_b/H_a$*100%

Preferably, the structured surfactant composition comprises less than 10% "third-phase" volume after rapid aging stability protocol. More preferably, the structured surfactant composition comprises less than 5% "third-phase" volume after rapid aging stability protocol. More preferably, the structured surfactant composition comprises less than 2% "third-phase" volume after rapid aging stability protocol. Even more preferably, the structured surfactant composition comprises less than 1% "third-phase" volume after rapid aging protocol. Most preferably, the structured surfactant composition comprises about 0% "third-phase" volume after rapid aging protocol.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

It should be understood that every maximum numerical limitation given throughout this specification will include every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A cleansing composition comprising:
   a. at least 5%, by weight of the composition, of a surfactant,
   b. at least about 25%, by weight of the composition, of water, and
   c. a cyclodextrin complex comprising a perfume, said perfume comprising a plurality of perfume raw materials, at least one of which is selected from iso-e super, methyl ionone, alpha-irone, gamma methyl ionone, labienone oxim, cashmeran, delta-damascone, beta-ionone, dihydro-beta-ionone, damascenone, and trans- and alpha-damascone;
   wherein 80% of the plurality of perfume raw materials comprise a FDV of at least 0.69.

2. The cleaning composition of claim 1, wherein the surfactant comprises sodium trideceth sulfate.

3. The cleansing composition of claim 1, further comprising at least one uncomplexed perfume.

4. The cleaning composition of claim 1, further comprising zinc pyrithione.

5. A cleansing composition for delivering a dilution triggered bloom of a perfume comprising:
   a. at least 5%, by weight of the composition, of a surfactant,
   b. at least about 25%, by weight of the composition, of water, and
   c. a cyclodextrin complex comprising a perfume, said perfume comprising perfume raw materials, at least one of which comprises a FDV of at least about 0.69;
   wherein the weight ratio of water to cyclodextrin complex is between about 15:1 and 1:1, and
   wherein the cyclodextrin complex has a degree of complexation of at least 90% prior to incorporation into the cleansing composition.

6. The cleansing composition of claim 5, wherein the cleansing composition comprises an ARDON value of at least about 130%.

7. The cleaning composition of claim 5, wherein the surfactant comprises sodium trideceth sulfate.

8. The cleansing composition of claim 7, further comprising at least one uncomplexed perfume.

9. The cleansing composition of claim 5, further comprising zinc pyrithione.

10. The cleansing composition of claim 5, further comprising at least one uncomplexed perfume.

11. The cleansing composition of claim 5, wherein the perfume raw materials comprise at least one of so-e super, methyl ionone, alpha-irone, gamma methyl ionone, labienone oxim, cashmeran, delta-damascone, beta ionone, dihydro-beta-ionone, damascenone, and trans- and alpha-damascone.

12. A cleansing composition comprising:
   a. at least 5%, by weight of the composition, of a surfactant,
   b. at least about 25%, by weight of the composition, of water, and
   c. a cyclodextrin complex comprising a perfume, said perfume comprising a plurality of perfume raw materials, at least one of which is selected from so-e super, methyl ionone, alpha-irone, gamma methyl ionone, labienone oxim, cashmeran, delta-damascone, beta-ionone, dihydro-beta-ionone, damascenone, and trans- and alpha-damascone;
   wherein 80% of the plurality of perfume raw materials comprise a FDV of at least 0.69,
   wherein the ratio of water to cyclodextrin complex is between about 15:1 and 1:1, and
   wherein the cleansing composition comprises a ARDON value of at least 130%.

13. The cleansing composition of claim 12, wherein the ARDON value is at least about 140%.

14. The cleaning composition of claim 12, wherein the surfactant comprises sodium trideceth sulfate.

15. The cleansing composition of claim 12, further comprising at least one uncomplexed perfume.

16. The cleaning composition of claim 12, further comprising zinc pyrithione.

17. The cleansing composition of claim 12, further comprising at least one uncomplexed perfume.

18. A cleansing composition comprising:
a. at least 5%, by weight of the composition, of a surfactant,
b. at least about 25%, by weight of the composition, of water, and
c. a cyclodextrin complex comprising a perfume, said perfume comprising a plurality of perfume raw materials, at least one of which is selected from iso-e super, methyl ionone, alpha-irone, gamma methyl ionone, labienone oxim, cashmeran, delta-damascone, beta-ionone, dihydro-beta-ionone, damascenone, and trans- and alpha-damascone;
wherein the cyclodextrin complex has a degree of complexation of at least 90% prior to incorporation into the cleansing composition.

19. A cleansing composition comprising:
a. at least 5%, by weight of the composition, of a surfactant,
b. at least about 25%, by weight of the composition, of water, and
c. a cyclodextrin complex comprising menthol;
wherein the cyclodextrin complex has a degree of complexation of at least 90% prior to incorporation into the cleansing composition.

20. The cleansing composition of claim 19, further comprising at least one anti-dandruff agent.

21. The cleansing composition of claim 20, wherein the at least one anti-dandruff agent is a pyridinethione salt.

\* \* \* \* \*